United States Patent
Weiand et al.

(10) Patent No.: US 9,273,162 B2
(45) Date of Patent: Mar. 1, 2016

(54) PROCESS FOR MONITORING THE POLYMERIZATION OF ETHYLENE OR ETHYLENE AND COMONOMERS IN A TUBULAR-REACTOR AT HIGH-PRESSURES

(75) Inventors: Sebastian Weiand, Cologne (DE); Wolfgang Gsella, Cologne (DE); Victor Kuhne, Cologne (DE); Christian-Ulrich Schmidt, Bonn (DE); Tom Zimmermann, Niederkassel (DE)

(73) Assignee: Basell Polyolefine GmbH, Wesseling (DE)

( * ) Notice: Subject to any disclaimer, the term of this patent is extended or adjusted under 35 U.S.C. 154(b) by 377 days.

(21) Appl. No.: 13/995,829

(22) PCT Filed: Dec. 19, 2011

(86) PCT No.: PCT/EP2011/073176
§ 371 (c)(1),
(2), (4) Date: Jun. 19, 2013

(87) PCT Pub. No.: WO2012/084772
PCT Pub. Date: Jun. 28, 2012

(65) Prior Publication Data
US 2013/0274424 A1    Oct. 17, 2013

Related U.S. Application Data

(60) Provisional application No. 61/439,205, filed on Feb. 3, 2011.

(30) Foreign Application Priority Data

Dec. 22, 2010   (EP) ..................................... 10015965

(51) Int. Cl.
*C08F 2/00* (2006.01)
*G01N 7/00* (2006.01)
(Continued)

(52) U.S. Cl.
CPC ...... *C08F 10/02* (2013.01); *G01N 7/00* (2013.01); *C08F 110/02* (2013.01); *C08F 210/02* (2013.01); *C08F 210/16* (2013.01); *C08F 2400/02* (2013.01)

(58) Field of Classification Search
CPC ............ C08F 10/02; C08F 2/00; C08F 2/001; C08F 110/02; C08F 210/02; C08F 210/16; C08F 2400/02; C08F 210/06; C08F 220/14; G01N 7/00
USPC .............................................. 526/64; 73/31.04
See application file for complete search history.

(56) References Cited

U.S. PATENT DOCUMENTS

| 3,284,432 A | 11/1966 | Mortimer |
| 5,100,978 A * | 3/1992 | Hasenbein ............. C08F 10/02 526/208 |

(Continued)

OTHER PUBLICATIONS

Zavala, Computers and Chemical Engineering, 1735-1746, May 5, 2009, Elsevier Ltd., Online publication.*

(Continued)

*Primary Examiner* — William Cheung

(57) ABSTRACT

A process for monitoring the polymerization of ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling the tubular reactor with a cooling medium, comprising a step of measuring as process parameters the temperature profile and the pressure of the reaction medium and the flow and temperature profile of the cooling medium along the reactor.

10 Claims, 1 Drawing Sheet

(51) Int. Cl.
*C08F 10/02* (2006.01)
*C08F 110/02* (2006.01)
*C08F 210/02* (2006.01)
*C08F 210/16* (2006.01)

(56) References Cited

U.S. PATENT DOCUMENTS

| | | |
|---|---|---|
| 6,144,897 A | 11/2000 | Selliers |
| 7,526,405 B2 | 4/2009 | Miller |
| 7,657,399 B2 | 2/2010 | Miller |
| 7,761,172 B2 | 7/2010 | Nguyen |
| 2003/0181632 A1 | 9/2003 | Maehling et al. |
| 2006/0167193 A1 | 7/2006 | Maehling et al. |
| 2007/0238844 A1 | 10/2007 | Lee et al. |
| 2012/0220738 A1 | 8/2012 | Mannebach et al. |
| 2012/0322956 A1 | 12/2012 | Schmidt et al. |

OTHER PUBLICATIONS

Cao et al: Control and modeling of temperature distribution in a tubular polymerization process, Computers & Chemical Engineering, Pergamon Press, Oxford, GB, vol. 31, No. 11, Aug. 25, 2007, pp. 1516-1524, XP022213307.

PCT International Search Report & Written Opinion mailed Mar. 26, 2012, for PCT/EP2011/073176.

Kiparissides, Chemical Engineering Science, 5011-5024, 1994, Elsevier Science Ltd., Great Britain.

* cited by examiner

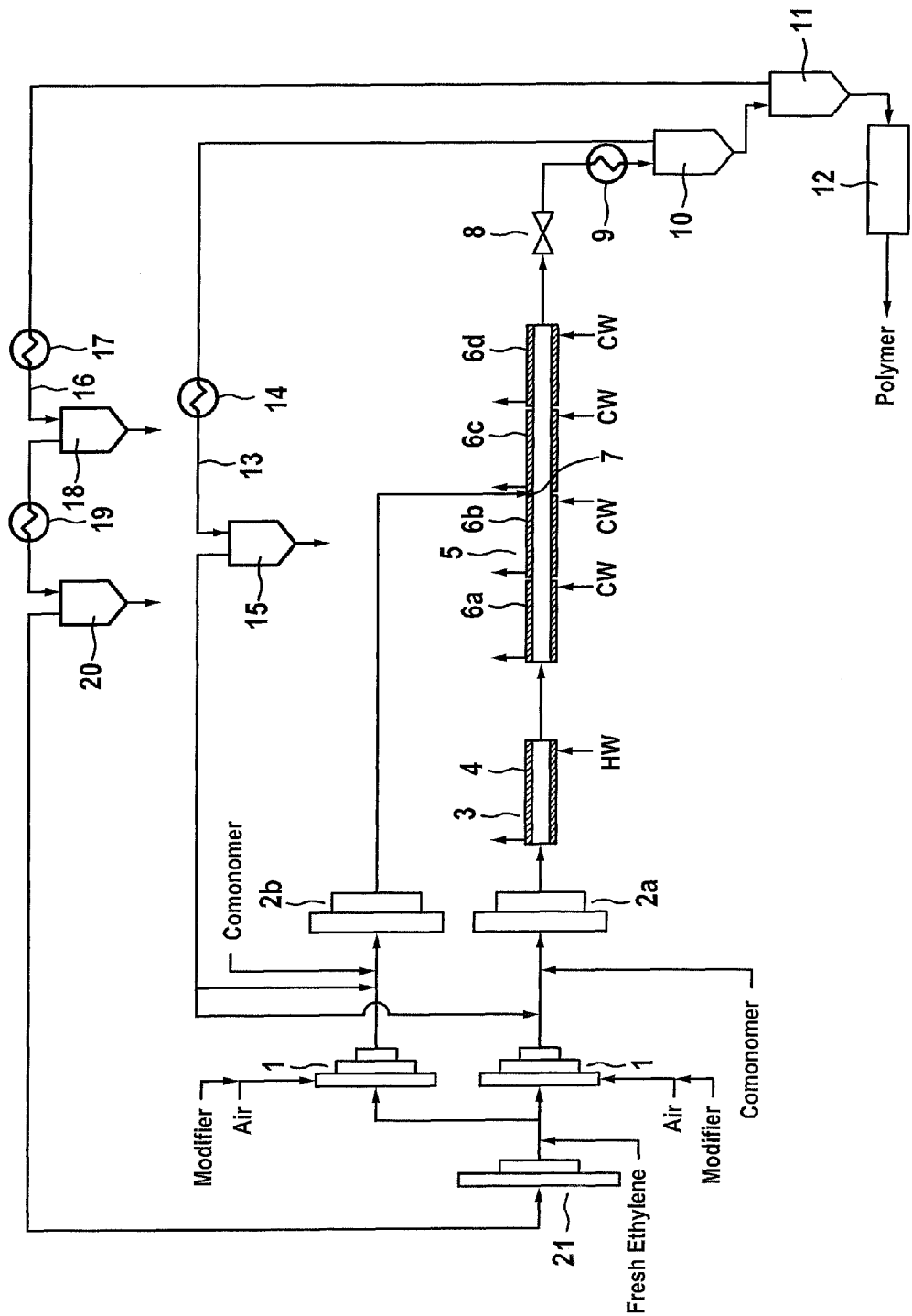

PROCESS FOR MONITORING THE POLYMERIZATION OF ETHYLENE OR ETHYLENE AND COMONOMERS IN A TUBULAR-REACTOR AT HIGH-PRESSURES

This application is the U.S. National Phase of PCT International Application PCT/EP2011/073176, filed Dec. 19, 2011, claiming priority of European Patent Application No. 10015965.6, filed Dec. 22, 2010 and the benefit under 35 U.S.C. 119(e) of U.S. Provisional Application No. 61/439, 205, filed Feb. 3, 2011, the contents of which are incorporated herein by reference in their entirety.

The present invention relates to a process for monitoring the polymerization of ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling the tubular reactor with a cooling medium, and to a process for polymerizing ethylene or ethylene and comonomers comprising such a monitoring process.

Polyethylene is the most widely used commercial polymer. It can be prepared by a couple of different processes. Polymerization in the presence of free-radical initiators at elevated pressures was the method first discovered to obtain polyethylene and continues to be a valued process with high commercial relevance for the preparation of low density polyethylene (LDPE). LDPE is a versatile polymer which can be used in a variety of applications, such as film, coating, molding, and wire and cable insulation. There is consequently still demand for optimizing the processes for its preparation.

A normal set-up for a tubular reactor LDPE plant consists essentially of a set of two compressors, a primary and a high pressure compressor, a tubular polymerization reactor and two separators for separating the monomer-polymer mixture leaving the tubular reactor, wherein in the first separator, the high pressure separator, the ethylene separated from the monomer-polymer mixture is recycled to the ethylene-feed between the primary compressor and the high pressure compressor, and the ethylene separated from the mixture in the second separator, the low pressure separator, is added to the stream of fresh ethylene before it is fed to the primary compressor. Such a high-pressure polymerization unit normally further includes apparatuses like extruders and granulators for pelletizing the obtained polymer. Monomer supply to the tubular reactor can either be carried out solely in the beginning of the reactor or only partly in the beginning with the other part fed via one or more side feed entries. Moreover, it is also common to introduce initiator in more than one place down the tube, thus creating more than one reaction zone.

The polymerization process in a tubular LDPE reactor is carried out at high pressures which can reach even 350 MPa. Such high pressure requires special technology for the process to be handled in a safe and reliable manner. Technical issues in handling ethylene at high pressures are, for example, described in Chem. Ing. Tech. 67 (1995), pages 862 to 864. It is stated that ethylene decomposes rapidly in an explosive manner under certain temperature and pressure conditions to give soot, methane and hydrogen. This undesired reaction occurs repeatedly in the high-pressure polymerization of ethylene. The drastic increase in pressure and temperature associated therewith represents a considerable potential risk for the operational safety of the production plants.

A possible solution for preventing a drastic increase in pressure and temperature of this type consists in installing rupture discs or emergency pressure-relief valves. WO 02/01308, for example, discloses a specific hydraulically controlled pressure relief valve which allows a particularly fast opening of the pressure relief valve in case of sudden changes in pressure or temperature. However, though it is technically possible to handle such thermal runaways or explosive decompositions of ethylene these situation are highly undesirable since they lead to a shut-down of the polymerization plant with frequent emission of ethylene into the environment and loss of production.

A possible solution for avoiding the risk of explosive decompositions of ethylene is carrying out the polymerization well below the decomposition limit. However, since the properties and the structure of the obtained ethylene homopolymers or copolymers, such as molecular weight, molecular weight distribution and the amount of short- and long-chain branching, depend strongly on the reaction parameters, restricting the polymerization to reaction temperatures which are very distant from the decomposition temperature means limiting the range of achievable products. Furthermore, the feasible ethylene conversion in a reaction zone depends on the amount of polymerization heat, which can be removed from the reaction mixture in the respective reaction zone. That means, the ethylene conversion is the higher the higher the peak polymerization temperature is. Because of these advantages of polymerizing at higher reaction temperatures there is a desire to be able to polymerize at temperatures as close to the decomposition temperature as possible however avoiding reliably any thermal runaway of the reaction mixture.

Consequently, it is an object of the present invention to overcome the mentioned hurdles and to find a process for polymerization ethylene or ethylene and comonomers in a tubular reactor which allows polymerizing with peak polymerization temperatures close to the decomposition limit but reduces or eliminates the risk of thermal runaway of the reaction mixture.

We have found that this object is achieved by a process for monitoring the polymerization of ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling the tubular reactor with a cooling medium, comprising the steps of a) measuring as process parameters the temperature profile and the pressure of the reaction medium and the flow and temperature profile of the cooling medium along the reactor, b) monitoring the feeds of ethylene, if present comonomer, free-radical polymerization initiator and chain-transfer agent to all reaction zones, c) calculating, based on the measured process parameters and on a model for the polymerization process, concentrations for free-radical polymerization initiator, chain-transfer agent, ethylene and, if present, comonomers at at least so many positions along the reactor, that at least one calculation is carried out all 10 s for a volume unit flowing through the reactor, d) calculating, based on the measured process parameters and the calculated concentrations, the cooling power, the generation of heat, and the concentration of radicals, e) calculating, based on the calculated data of the cooling power, of the generation of heat, and of the concentration of radicals, the potential of a thermal runaway of the reaction mixture at the positions along the reactor which have the highest temperatures, and f) outputting an alarm signal if the calculated value for the potential of a thermal runaway a predefined value.

Furthermore, we have found a process for polymerizing ethylene or ethylene and comonomers comprising such a monitoring process.

The features and advantages of the present invention can be better understood via the following description and the accompanying drawing which shows schematically the set-up of a tubular polymerization reactor according to the process of the present invention.

The process of the invention can be used both for the homopolymerization of ethylene and for the copolymerization of ethylene with one or more other monomers, provided that these monomers are free-radically copolymerizable with ethylene under high pressure. Examples of suitable copolymerizable monomers are α,β-unsaturated $C_3$-$C_8$-carboxylic acids, in particular maleic acid, fumaric acid, itaconic acid, acrylic acid, methacrylic acid and crotonic acid, derivatives of α,β-unsaturated $C_3$-$C_8$-carboxylic acids, e.g. unsaturated $C_3$-$C_{15}$-carboxylic esters, in particular esters of $C_1$-$C_6$-alkanols, or anhydrides, in particular methyl methacrylate, ethyl methacrylate, n-butyl methacrylate or tert-butyl methacrylate, methyl acrylate, ethyl acrylate, n-butyl acrylate, 2-ethylhexyl acrylate, tert-butyl acrylate, methacrylic anhydride, maleic anhydride or itaconic anhydride, and 1-olefins such as propene, 1-butene, 1-pentene, 1-hexene, 1-octene or 1-decene. In addition, vinyl carboxylates, particularly preferably vinyl acetate, can be used as comonomers. Propene, 1-hexene, acrylic acid, n-butyl acrylate, tert-butyl acrylate, 2-ethylhexyl acrylate, vinyl acetate or vinyl propionate are particularly advantageously used as comonomer.

In the case of copolymerization, the proportion of comonomer or comonomers in the reaction mixture is from 1 to 45% by weight, preferably from 3 to 30% by weight, based on the amount of monomers, i.e. the sum of ethylene and other monomers. Depending on the type of comonomer, it can be preferred to feed the comonomers at a plurality of different points to the reactor.

For the purposes of the present invention, polymers are all substances which are made up of at least two monomer units. They are preferably LDPE polymers having an average molecular weight $M_n$ of more than 20 000 g/mole. However, the method of the invention can also be advantageously employed in the preparation of oligomers, waxes and polymers having a molecular weight $M_n$ of less than 20 000 g/mole.

The process of the present invention is suitable for monitoring polymerizations carried out with all kinds of free-radical polymerization initiators such as oxygen, air, azo compounds or peroxidic polymerization initiators. The process is especially suitable for polymerizations using oxygen, either fed in the form of pure $O_2$ or as air, because when using oxygen as initiator there is still a significant amount of initiator decomposing at peak temperature resulting in a relatively broad temperature range in which the decomposition limit can be. In case of initiating the polymerization with oxygen, the initiator is normally first mixed with the ethylene feed and then fed to the reactor. In preferred embodiments to the process such a stream comprising monomer and oxygen is not only fed to the beginning of the tubular reactor but also to one or more points along the reactor creating two or more reaction zones.

Examples of suitable organic peroxides are peroxy esters, peroxy ketals, peroxy ketones and peroxycarbonates, e.g. di(2-ethylhexyl) peroxydicarbonate, dicyclohexyl peroxydicarbonate, di-acetyl peroxydicarbonate, tert-butyl peroxyisopropylcarbonate, di-tert-butyl peroxide, di-tert-amyl peroxide, dicumyl peroxide, 2,5-dimethyl-2,5-di-tert-butylperoxyhexane, tert butyl cumyl peroxide, 2,5-dimethyl-2,5-di(tert-butylperoxy)hex-3-yne, 1,3-diisopropyl monohydroperoxide or tert-butyl hydroperoxide, didecanoyl peroxide, 2,5-dimethyl-2,5-di(2-ethylhexanoylperoxy)hexane, tert-amyl peroxy-2-ethylhexanoate, dibenzoyl peroxide, tert butyl peroxy-2 ethyl-hexanoate, tert-butyl peroxydiethylacetate, tert-butyl peroxydiethylisobutyrate, tert-butyl peroxy-3,5,5-trimethylhexanoate, 1,1-di(tert-butylperoxy)-3,3,5-trimethylcyclohexane, 1,1-di(tert-butylperoxy)cyclohexane, tert butyl peroxyacetate, cumyl peroxyneodecanoate, tert-amyl peroxyneodecanoate, tert-amyl peroxypivalate, tert-butyl peroxyneodecanoate, tert-butyl permaleate, tert-butyl peroxypivalate, tert-butyl peroxyisononanoate, diisopropylbenzene hydroperoxide, cumene hydroperoxide, tert butyl peroxybenzoate, methyl isobutyl ketone hydroperoxide, 3,6,9-triethyl-3,6,9-trimethyl-triperoxocyclononane and 2,2-di(tert-butylperoxy)butane. Azoalkanes (diazenes), azodicarboxylic esters, azodicarboxylic dinitriles such as azobisisobutyronitrile and hydrocarbons which decompose into free radicals and are also referred as C—C initiators, e.g. 1,2-diphenyl-1,2-dimethylethane derivatives and 1,1,2,2-tetramethylethane derivatives, are also suitable. It is possible to use either individual initiators or preferably mixtures of various initiators. A large range of initiators, in particular peroxides, are commercially available, for example the products of Akzo Nobel offered under the trade names Trigonox® or Perkadox®.

In a preferred embodiment of the process of the invention, peroxidic polymerization initiators having a relatively high decomposition temperature are used. Suitable peroxidic polymerization initiators include, for example, 1,1-di(tert-butylperoxy)cyclohexane, 2,2-di(tert-butylperoxy)butane, tert-butyl peroxy-3,5,5-trimethylhexanoate, tert-butyl peroxybenzoate, 2,5-dimethyl-2,5-di(tert-butylperoxy)hexane, tert-butyl cumyl peroxide, di-tert-butyl peroxide and 2,5-dimethyl-2,5-di(tert-butylperoxy)hex-3-yne, and particular preference is given to using di-tert-butyl peroxide.

The initiators can be employed individually or as a mixture in concentrations of from 0.1 to 50 mol/t of polyethylene produced, in particular from 0.2 to 20 mol/t, in each reaction zone. Preferably mixtures of at least two different azo compounds or organic peroxides are used. There is no limit for the number of different initiators in such a mixture, however preferably the mixtures are composed of from two to six and in particular of four or five different initiators. Particular preference is given to using mixtures of initiators which have different decomposition temperatures.

It is often advantageous to use the initiators in the dissolved state. Examples of suitable solvents are ketones and aliphatic hydrocarbons, in particular octane, decane and isododecane and also other saturated $C_5$-$C_{25}$-hydrocarbons. The solutions comprise the initiators or initiator mixtures in proportions of from 2 to 65% by weight, preferably from 5 to 40% by weight and particularly preferably from 10 to 30% by weight.

In the process of the invention, the molecular weight of the polymers to be prepared can as usual be altered by addition of modifiers which act as chain-transfers agents. Examples of suitable modifiers are hydrogen, aliphatic and olefinic hydrocarbons, e.g. pentane, hexane, cyclohexane, propene, 1-pentene or 1-hexene, ketones such as acetone, methyl ethyl ketone (2-butanone), methyl isobutyl ketone, methyl isoamyl ketone, diethyl ketone or diamyl ketone, aldehydes such as formaldehyde, acetaldehyde or propionaldehyde and saturated aliphatic alcohols such as methanol, ethanol, propanol, isopropanol or butanol. Particular preference is given to using saturated aliphatic aldehydes, in particular propionaldehyde or 1-olefins such as propene or 1-hexene.

The reaction mixture generally comprises polyethylene in an amount in the range of from 0 to 45% by weight, based on the total monomer-polymer mixture, preferably from 0 to 35% by weight.

The process of the invention is carried out at pressures of from 160 MPa to 350 MPa, with pressures of from 180 MPa to 340 MPa being preferred and pressures of from 200 MPa to 330 MPa being particularly preferred. The temperatures are in the range from 100° C. to 350° C., preferably from 120° C. to 340° C. and very particularly preferably from 150° C. to 320° C. In the case of copolymerization of ethylene with sensitive or strongly regulating comonomers, in particular free radically polymerizable carboxylic esters, e.g. vinyl esters, the polymerization is preferably carried out at temperatures below 230° C. In general, preference is given to a process in which the polymerization temperature is not higher than 320° C.

The process of the present invention can be carried out with all types of tubular reactors suitable for high-pressure polymerization having one or more reaction zones, preferably from 2 to 6 reaction zones and particularly preferably from 2 to 4 reaction zones. The number of reaction zones is given by the number of feeding points for the initiator. Such a feeding point can be an injection point for a solution of azo compounds or organic peroxides or a side feed of cold ethylene comprising oxygen or other free-radical polymerization initiator. In all these cases fresh initiator is added to the reactor, where it decomposes into free radicals and initiates further polymerization. Usually each reaction zone is followed by a zone of the tubular reactor in which only cooling of the reaction mixture occurs.

Suitable tubular reactors are basically long, thick-walled pipes, which are usually from about 0.5 km to 4 km, preferably from 1.5 km to 3 km and especially from 2 km to 2.5 km long. The inner diameter of the pipes is usually in the range of from about 30 mm to 120 mm and preferably from 60 mm to 90 mm. Such tubular reactors have preferably a length-to-diameter ratio of greater than 1000, preferably from 10000 to 40000 and especially from 25000 to 35000.

The flow rate is usually in the range of from 5 m/s to 30 m/s and preferably from 10 m/s to 20 m/s. The production rate varies strongly with the size of the plant and the product mix and can be in the range of from 3 t/h to 50 t/h or even higher.

THE BRIEF DESCRIPTION OF THE FIGURE

FIG. 1 shows a typical set-up for a preferred tubular polymerization reactor without however restricting the invention to the embodiments described therein.

The fresh ethylene, which is usually under a pressure of 1.7 MPa, is firstly compressed to a pressure of about 30 MPa by means of two primary compressors (1) and then compressed to the reaction pressure of about 300 MPa using two high pressure compressors (2a) and (2b). The molecular weight regulator and air as oxygen source are added to the primary compressors (1). The reaction mixture leaving the high pressure compressor (2a) is fed to a pre-heater (3), which is equipped with a heating jacket (4), to which a heating medium, preferably hot water or steam HW, of a temperature of from about 150 to 250° C. is fed. The reaction mixture is heated in the pre-heater (3) to the reaction start temperature of from about 120° C. to 220° C. and then conveyed to the tubular reactor (5).

The tubular reactor (5) is equipped with a cooling jacket to remove the liberated heat of reaction from the reaction mixture by means of a cooling medium, preferably cooling water CW, of a temperature from about 100 to 220° C. The cooling jacket is divided in four sections (6a) to (6d), which are all separately fed with the cooling medium. Possible other preferred layouts for the cooling jacket could be that it is divided in six, eight or ten sections with are individually provided with cooling water.

The reaction mixture leaving the high pressure compressor (2b) is fed as cold mixture to the tubular reactor (5) at point (7). The feed of the additional oxygen starts further polymerization downstream of point (7), thus creating a second reaction zone. There could also be additional points along the tubular reactor to which cold reaction mixture is fed. Preferably the number of side feeds to reactor is from 1 to 4 and in particular 1 or 2 and most preferably 1.

The reaction mixture leaves the tubular reactor (5) through a high-pressure let-down valve (8) and passes a post reactor cooler (9). Thereafter, the resulting polymer is separated off from unreacted ethylene and other low molecular weight compounds (monomers, oligomers, polymers, additives, solvent, etc.) by means of a high-pressure separator (10) and a low-pressure separator (11), discharged and pelletized via an extruder and granulator (12).

The ethylene which has been separated off in the high-pressure separator (10) is fed back to the inlet end of the tube reactor (5) in the high-pressure circuit (13) at 30 MPa. It is first freed from other constituents in at least one purification stage and then added to the monomer stream between primary compressors (1) and high pressure compressors (2a) and (2b). FIG. 1 shows one purification stage consisting of a heat exchanger (14) and a separator (15). It is however also possible to use a plurality of purification stages. The high-pressure circuit (13) usually separates waxes.

The ethylene which has been separated off in the low-pressure separator (11), which further comprises, inter alia, the major part of the low molecular weight products of the polymerization (oligomers) and the solvent of the initiators, is worked up in the low-pressure circuit (16) at a pressure of from about 0.1 to 0.4 MPa in a plurality of separators with a heat exchanger being located between each of the separators and then fed to a booster compressor (21), in which it is compressed to a pressure of about 1.7 MPa and then conveyed to primary compressors (1). FIG. 1 shows two purification stages consisting of heat exchangers (17) and (19) and separators (18) and (20). It is however also possible to use only one purification stages or preferably more than two purification stages. The low-pressure circuit (16) usually separates oil and waxes.

Different configurations for suitable tubular polymerization reactor are of course also possible, for example for a set-up with feeding solutions of azo compounds or organic peroxides or their mixtures. In such cases the number of initiator injection points and reaction zones is usually from 2 to 6 and preferably 2, 3 or 4 and most preferably 4.

According to the present invention the polymerisation is monitored by a process which outputs an alarm signal if the risk of a thermal runaway exceeds a certain level. This process comprises a step of measuring the temperature profile and the pressure of the reaction medium and the flow and temperature profile of the cooling medium along the reactor.

Measuring these data has to be carried out with a sufficient accuracy. Furthermore, it is needed to have an adequate number of temperature measuring devices along the reactor in order to determine the temperature profile sufficiently precise. Preferably the reactor is equipped at least every 50 m, more preferably at least every 40 m, particular preferred at least every 30 m, and especially every 20 m with a temperature measuring device for measuring the temperature of the reaction medium. Preferred means for measuring the temperature of the reaction medium are for example thermocouples as described in WO 97/25601. Preferably the means for measuring the temperature of the reaction medium have a relative failure of the temperature measurements of not more than 3% of the measuring range, more preferably not more than 2% of the measuring range and especially not more than 1.5% of the measuring range.

Preferably the devices for measuring the temperature of the cooling medium are located at the same positions as the devices for measuring the temperature of the reaction medium and are accordingly also preferably located at least every 50 m, more preferably at least every 40 m, particular preferred at least every 30 m, and especially every 20 m. Preferred means for measuring the temperature of the reaction medium are for example PT-100 thermometers. Preferably the means for measuring the temperature of the cooling medium have a relative failure of the temperature measurements of not more than 2% of the measuring range, more preferably not more than 1.5% of the measuring range and especially not more than 1% of the measuring range.

The flow of the cooling medium in the six sections of the cooling jacket, preferably hot water, is preferably determined by flow meters. Such flow meters have preferably a relative failure of not more than 10% of the measuring range and especially not more than 5% of the measuring range. The pressure inside the reactor is preferably determined by pressure sensors, preferably a positions in the beginning, in the middle, preferably near the location of a side feed, and/or in the end of the tubular reactor. The feeds of ethylene, if present comonomer, free-radical polymerization initiator and chain-transfer agent to all reaction zones are preferably measured via flow meters with a relative failure of preferably not more than 15% of the measuring range, more preferably not more than 10% of the measuring range and particularly not more than 5% of the measuring range.

Taking the measured process data as parameters, concentrations of free-radical polymerization initiator, chain-transfer agent, ethylene and, if present, comonomers are calculated along the reactor based on a model for the polymerization process. Preferably the model is a first principle model which uses implicit differential equations and iterative calculation procedures for describing the conditions inside the tubular reactor and the interaction of different parts of the LDPE plant. Preferably such a model combines a classic reaction model, which describes the whole polymerization reaction including decomposition of oxygen, chain propagation, chain termination, backbiting and chain transfer and the occurrence of heat and mass transfer phenomena, with a model describing the thermal self initiation of monomer. Especially preferred models for the polymerization process consist of kinetic and thermodynamic balances and take into account mass transport phenomena. The conversion of the different educts is preferably calculated with a reduced kinetic model which uses a heat balance to estimate the production of LDPE in a reactor volume unit and correlates the production of LDPE with the consumption of initiator, chain-transfer agent, ethylene and, if present, comonomer.

The calculation of the concentrations has to be fast enough to be solved online during plant operation, i.e. within a limited cycle time. Accordingly, the concentrations of free-radical polymerization initiator, chain-transfer agent, ethylene and, if present, comonomers are usually calculated every minute, preferably every 30 s, more preferably every 15 s and in particular every 5 s.

There are at least so many calculations carried out at positions along the reactor that, for a volume unit flowing through the reactor, there is made at least one calculation all 10 seconds and preferably all 5 seconds. That means, the distance of the positions along the tubular reactor, where a calculation is carried out, has to be so that, for a given flow rate, the time for a volume unit flowing through the reactor has to be less than 10 seconds until the next position is reached where a further calculation is carried out. That means, for example, if the flow rate is 10 m/s the distance between two positions, where a calculation is carried out, has to be less than 100 m and preferably less than 50 m.

Based on these calculated concentrations of free-radical polymerization initiator, chain-transfer agent, ethylene and, if present, comonomers and on measured process parameters the cooling power, the generation of heat, and the concentration of radicals is calculated. The cooling power is preferably calculated via the heat balance of the cooling medium. The generation of heat is preferably calculated by using the measured reactor temperatures taking into account the cooling power. The amount of generated heat in combination with the known molecular weight is used to estimate the concentration of radicals over the length of the reactor. Preferably the model for the polymerization process has been refined by adjusting it to factual conditions measured in the LDPE plant.

At the positions along the reactor having the highest temperatures, the potential of a thermal runaway of the reaction mixture is then calculated based on the data obtained in the previous calculation steps. For this purpose the conditions at these positions have preferably been compared with the conditions at such positions, which had previously been recorded in the LPPE plant in situations shortly before and during a thermal runaway of the reaction mixture.

In case the calculated value for the potential of thermal runaway exceeds a predefined value an alarm signal is output. Preferably the output alarm signal is brought to the attention of the shift personal, which is operating the polymerization reactor.

In a preferred embodiment of the present invention two kinds of alarm signal are output, a first level alarm signal, which indicates that the reaction system is close to the limit of decomposition at at least one point in the polymerization reactor, and a second level alarm signal, which indicates that the reaction system is at at least one point in the polymerization reactor within decomposition limit and a small variation of any process parameter can result immediately in a thermal runaway.

The monitoring process according to the present invention can advantageously be used in processes for polymerization ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling with a cooling medium at each reaction zone.

By running the high-pressure tubular reactor polymerization plant with the monitoring process of the present invention it is possible to drastically reduce the factual number of thermal runaways in the polymerization of ethylene or ethylene and comonomers.

The invention is illustrated below with the aid of an example, without being restricted thereto.

EXAMPLE

The process for monitoring the polymerization of ethylene or ethylene and comonomers according to the present invention was applied to a high-pressure polymerization unit comprising a tubular high-pressure reactor operating with oxygen as free-radical polymerization initiator. The reactor had the general design shown in FIG. 1 with air being used as oxygen source. Fresh ethylene admixed with oxygen and modifier was not only fed to the beginning of the tubular reactor but also as cooled stream to the middle of the polymerization reactor. Accordingly the tubular reactor had two reaction zones. The cooling jacket was dived in six sections, which were separately supplied with hot water as cooling medium. Thus, each reaction zone was cooled by three sections of the cooling jacket. The tubular reactor had in total a length of 1000 m, a diameter of 45 mm in the first reaction zone and a diameter of 55 mm in the second reaction zone. The ethylene feed to the reactor was 20 t/h. Propionaldehyde was used as chain-transfer agent or modifier in an amount of from 0.5 to 5 kg/t of produced polyethylene. The polyethylene output varied with the produced LDPE grade, it was however always in the range of from 3 to 5 metric tons/h. The reactor inlet pressure was varied in the range of from 210 to 320 MPa.

For measuring the temperature profile the reaction medium the tubular reactor was equipped every 25 m with thermocouples of an accuracy of 2% of the measuring range. At the same positions also the cooling jacket was equipped with PT-100 thermometers of an accuracy of 1% of the measuring range for measuring the temperature profile of the cooling medium. The pressure inside the reactor and the flow in the six sections of the cooling jacket were determined directly by pressure sensors and flow meters.

The information about feed of ethylene, if present, comonomer, air and propionaldehyde was obtained directly via flow meters in the respective dosing systems.

At the positions of measuring the temperatures of reaction medium and water in the cooling jacket, that means every 25 m along the reactor, the concentrations of free-radical polymerization initiator, chain-transfer agent, ethylene and, if present, comonomer were calculated. With a flow rate of the reaction medium in the tubular reactor of 5 m/s in the first reaction zone and a flow rate of the reaction medium of 6 m/s in the second reaction zone this corresponds to calculating these concentrations all 5 s for a volume unit flowing through the reactor in the first reaction zone and all 4 s for a volume unit flowing through the reactor in the second reaction zone. The calculation was carried out on the basis of a first principle model using implicit differential equations and iterative calculation procedures for describing the conditions inside the tubular reactor. The first principle model combined a classic reaction model which describes the whole polymerization reaction (decomposition of oxygen; chain propagation; chain termination; backbiting; chain transfer) and the occurrence of heat and mass transfer phenomena with a model describing the thermal self initiation of monomer. The data for mass flows, concentration in the feed streams and temperatures and pressures were fed as inputs to the first principle model.

Based on the obtained values for the concentrations of components of the reaction mixture at these positions the concentration of free radicals, the generation of heat and the cooling power were calculated for all these positions.

For obtaining the information about the potential of a thermal runaway of the reaction mixture, the conditions at positions with the highest temperatures were compared with the conditions at such positions, which had previously been recorded in the polymerization unit in situations shortly before and during a thermal runaway of the reaction mixture. This calculation of the potential of the thermal runaway of the reaction mixture was repeated at least every 30 s so that a real online monitoring of the polymerization was achieved.

In case the actual process conditions were approaching the limit of decomposition the calculation tool gave an alarm to the shift personal operating the plant to allow them altering the reaction conditions.

By running the high-pressure tubular reactor polymerization plant with the monitoring process of the present invention for 1 year producing nine different LDPE grades it was possible to reduce the number of shut-downs caused by thermal runaway of the reaction mixture to 3, compared to 13 shut-downs caused by thermal runaway of the reaction mixture in the same time period before with the identical product split, however without carrying out the monitoring process of the present invention.

What is claimed is:

1. A process for monitoring the polymerization of ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling the tubular reactor with a cooling medium, comprising the steps of
   a) measuring as process parameters the temperature profile and the pressure of the reaction medium and the flow and temperature profile of the cooling medium along the reactor,
   b) monitoring the feeds of ethylene, comonomer, free-radical polymerization initiator and chain-transfer agent to all reaction zones,
   c) calculating, based on the measured process parameters and on a model for the polymerization process, concentrations for free-radical polymerization initiator, chain-transfer agent, ethylene and comonomers at at least so many positions along the reactor, that at least one calculation is carried out all 10 s for a volume unit flowing through the reactor,
   d) calculating, based on the measured process parameters and the calculated concentrations, the cooling power, the generation of heat, and the concentration of radicals,
   e) calculating, based on the calculated data of the cooling power, of the generation of heat, and of the concentration of radicals, the potential of a thermal runaway of the reaction mixture at the positions along the reactor which have the highest temperatures, and
   f) outputting an alarm signal if the calculated value for the potential of a thermal runaway exceeds a predefined value.

2. A process according to claim 1, wherein the model for the polymerization process consists of kinetic and thermodynamic balances and takes into account mass transport phenomena.

3. A process according to claim 2, wherein the model for the polymerization process has been refined by adjusting the model to factual reactor conditions shortly before and during a thermal runaway of the reaction mixture.

4. A process according to claim 1, wherein the relative failure of the devices for measuring the temperature of the reaction medium is not more than 3% of the measuring range.

5. A process according to claim 1, wherein relative failure of the devices for measuring the temperature of the cooling medium is not more than 2% of the measuring range.

6. A process according to claim 1, wherein the free-radical polymerization initiator is oxygen.

7. A process according to claim 1, wherein ethylene is copolymerized with one or more comonomers selected from the group consisting of propene, 1-hexene, acrylic acid, n-butyl acrylate, tert-butyl acrylate, 2-ethylhexyl acrylate, vinyl acetate and vinyl propionate.

8. A process according to claim 1, wherein the output alarm signal is brought to the attention of the shift personal, which is operating the polymerization reactor.

9. A process according to claim 1, wherein two kinds of alarm signal are output, a first level alarm signal, which indicates that the reaction system is close to the limit of decomposition at at least one point in the polymerization reactor, and a second level alarm signal, which indicates that the reaction system is at at least one point in the polymerization reactor within decomposition limit and a small variation of any process parameter can result immediately in a thermal runaway.

10. A process for polymerizing ethylene or ethylene and comonomers in the presence of free-radical polymerization initiator at pressures in the range of from 160 MPa to 350 MPa and temperatures in the range of from 100° C. to 350° C. in a tubular reactor with one or more reaction zones, which is equipped with cooling jackets for cooling with a cooling medium at each reaction zone, comprising a monitoring process according to claim 1.

\* \* \* \* \*